United States Patent [19]

Yamano

[11] 4,003,661
[45] Jan. 18, 1977

[54] APPARATUS FOR DETECTING CONTAMINATION OF LIQUID

[75] Inventor: Shigemi Yamano, Isehara, Japan

[73] Assignee: Kabushiki Kaisha Komatsu Seisakusho, Tokyo, Japan

[22] Filed: July 23, 1975

[21] Appl. No.: 598,346

[30] Foreign Application Priority Data

July 26, 1974 Japan .............................. 49-86364
Nov. 13, 1974 Japan ............................ 49-130617

[52] U.S. Cl. ................................ 356/201; 356/70; 356/208; 356/244
[51] Int. Cl.[2] ........................................ G01N 33/28
[58] Field of Search ............ 356/70, 201, 208, 244, 356/246

[56] References Cited
UNITED STATES PATENTS

| 1,999,889 | 4/1935 | Anselmi | 356/246 |
| 3,194,111 | 7/1965 | Saunders | 356/246 |
| 3,744,907 | 7/1973 | Whelan | 356/70 |
| 3,829,217 | 8/1974 | Johnson et al. | 356/70 |

Primary Examiner—John K. Corbin
Assistant Examiner—Richard A. Rosenberger
Attorney, Agent, or Firm—Spensley, Horn & Lubitz

[57] ABSTRACT

In apparatus for detecting the degree of contamination of liquid of the type wherein the quantity of light transmitting through a liquid sample is detected, a combination of a transparent flat plate and a convex lens is interposed between a light source and a light receiver. The flat plate is in contact with the convex lens at the top of the convex lens so as to define an annular gap for accommodating the liquid sample.

5 Claims, 11 Drawing Figures

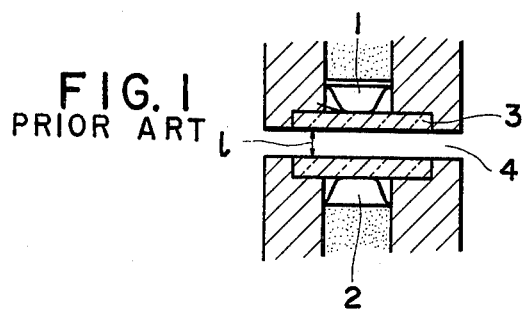
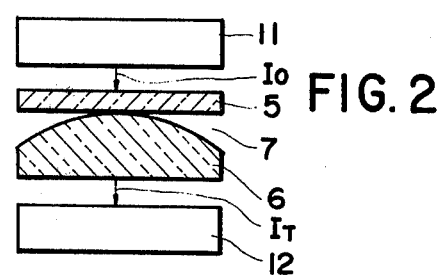
FIG. 1 PRIOR ART
FIG. 2
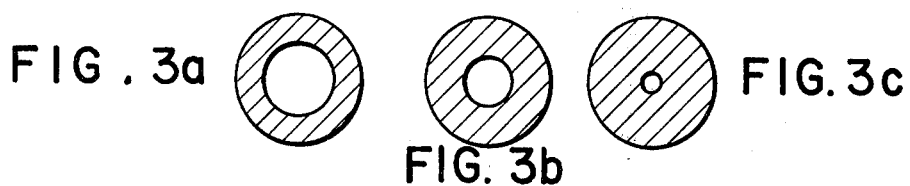
FIG. 3a   FIG. 3b   FIG. 3c
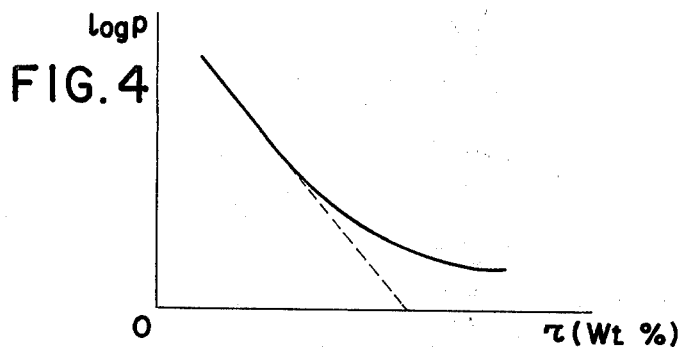
FIG. 4
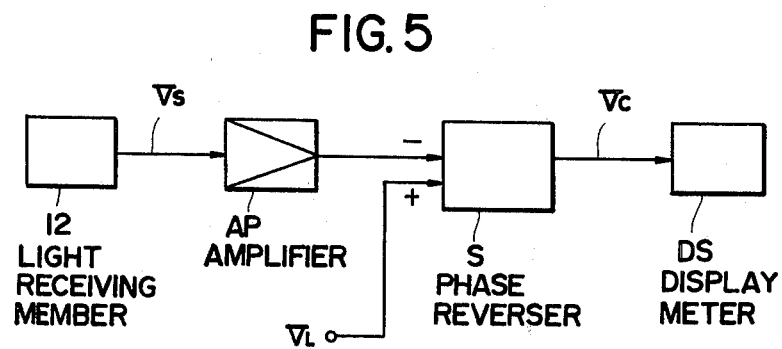
FIG. 5

APPARATUS FOR DETECTING CONTAMINATION OF LIQUID

BACKGROUND OF THE INVENTION

This invention relates to apparatus for detecting contamination of liquid, and, more particularly, apparatus for detecting contamination of liquid suitable for detecting the quantity of a component insoluble to a solvent such as benzene and contained in engine oil utilized in a diesel engine for operating a bulldozer, for instance.

In a prior art apparatus for measuring the degree of contamination of oil comprises a light emitting member 1, a light receiving member 2 and transparent members 3 for defining therebetween a space 4 having a definite width $l$ as shown in FIG. 1, and a sample of oil is passed through the gap to measure the quantity of the light transmitting through the space 4 thereby determining the degree of contamination of the oil. When the degree of contamination of the oil exceeds 2.5 w/% which is specified as the quantity of the component insoluble to benzene, it is necessary to exchange the oil. The thickness of the oil sample, that is, the width $l$ of the space 4, is generally maintained at about 1 mm.

However, as the engine oil of a diesel engine utilized to drive a bulldozer or the like contains a large quantity of carbon it is impossible to accurately measure the degree of contamination with a measuring width $l$ of about 1 mm. Although the degree of contamination can be measured by decreasing the width $l$ to about 0.01 mm, it is impossible to maintain the measuring width at this value since the temperature of the engine oil varies from 0° to 120° C, especially at the pistons from 0° to 340° C.

Moreover, the reliability and accuracy of the prior art apparatus are impaired by variations in the quantity of the light emanated from the lights source owing to difference in characteristics of the light source and aging of the luminous element. For example, the variation in the quantity of light emanated by a luminous diode amounts to ± 20 % per year due to aging. Accordingly, there is a defect that it is impossible to accurately measure the degree of contamination of liquid due to the variations in the characteristics of the light source.

SUMMARY OF THE INVENTION

It is an object of this invention to provide an improved apparatus capable of accurately detecting the degree of contamination of liquid which is contaminated to such a heavy extent that light transmission is made difficult.

Another object of this invention is to provide a novel apparatus for detecting contamination of a liquid sample which can maintain the quantity of light emanated from a light source at a constant value by compensating the variation of the light quantity due to difference in the characteristic of the light source of aging thereof, thereby accurately detecting the quantity of the light transmitting through the sample, which is a measure of the degree of contamination.

Still another object of this invention is to provide a novel apparatus for detecting the contamination of a liquid saple which is convenient for transport and can promptly detect the degree of contamination by using extremely small quantity of the sample.

According to this invention, there is provided apparatus for detecting contamination of liquid of the type wherein light emanated by a luminous element is transmitted through a liquid sample and the quantity of the transmitted light is detected by a light receiving member, characterized in that a pair of transparent members is interposed between the luminous element and the light receiving member, and that at least one of the transparent members is convex and in contact with the other at the top of the convex member thus forming therebetween a gap for accomodating a liquid sample.

According to a modified embodiment, for the purpose of compensating for the variation in the quantity of light emanated by the light source due to aging or difference in the characteristics thereof there is provided a compensating means including a photoelectric converting element for detecting the quantity of light emanated by the light source before the light transmits through the transparent members, means for generating a desired luminous quantity setting signal, a comparator for comparing the setting signal with the output from the photoelectric converting element and means responsive to the output from the comparator for controlling the quantity of the light emanated by the light source at a constant value corresponding to the luminous quantity setting signal.

BRIEF DESCRIPTION OF THE DRAWINGS

This invention can be more fully understood from the following detailed description taken in conjunction with the accompanying drawings in which:

FIG. 1 is sectional view showing one example of prior art apparatus for detecting contamination of oil or the like liquid.

FIG. 2 is a diagrammatic sectional view showing the optical measuring system of the apparatus for detecting contamination of oil embodying the invention;

FIGS. 3a, 3b and 3c are plan views showing the variation in the diameter of transmission circules;

FIG. 4 is a graph determined by an experimental equation and showing the relationship between the quantity of the light transmitted and the degree of contamination;

FIG. 5 is a block diagram of a circuit for displaying an output signal produced by a light receiving element;

DESCRIPTION OF THE PREFERRED EMBODIMENTS

Figure 6:
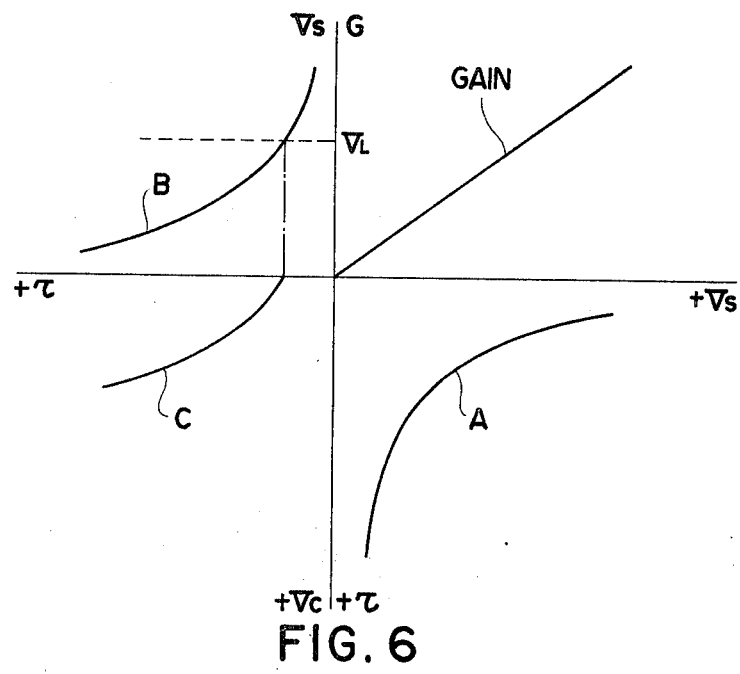
FIG. 6 is a graph showing the output characteristics of various elements utilized in the circuit shown in FIG. 5.

The principle of the invention and one embodiment thereof will now be described with reference to FIGS. 2, 3 and 4. As shown in FIG. 2, a transparent flat plate 5, made of glass for example, and a convex lens 6 having a flat bottom are in contact with each other to form a gap 7 therebetween and a sample (not shown) of deteriorated or contaminated oil is filled in the gap 7 at the time of measurement.

A luminous element 11 such as luminous diode 11 is placed above the assembly for transmitting parallel light through the transparent flat plate 5. As the bottom surface of the flat plate 5 is in contact with the top of the convex lens 6 the optical path length in the sample increases according to the secondary curve having the origin at the contact point. Accordingly, even when a heavily contaminated liquid sample containing carbon, for example, is tested, it is possible to assure sufficient quantity of light transmission at the narrow portion of the gap 7. Further, the flow of the oil sample is made easy at the periphery of the gap where the optical path length is large.

As the quantity of the component contained in the oil which is insoluble to benzine increases, the diameter of the transmission circle decreases as shown by FIGS. 3a, 3b and 3c in which unshaded portions show the transmission circle. On the other hand, when the quantity of the component insoluble to benzene decreases, the diameter of the transmission circle increases from FIG. 3c to FIG. 3a through FIG. 3b.

When the sample is filled in the gap 7 between the flat plate 5 and the convex lens 6, the quantity P of the light transmitted is expressed by the following equation when the convex lens is assumed to be circular.

$$P = \pi \left\{ -\frac{1}{\tau \log e} c \int_a^b (\log I_T - \log T_0) \, dI_T - \frac{1}{\tau (\log e)^2} \int_a^b (\log I_T - \log I_0)^2 \, dI_T \right\} \quad (1)$$

where $\tau$ represents the quantity of the component insoluble to a solvent, $a$ the intensity of the transmission light at a point spaced by R from the optical axis, $b$ the intensity of the incident light ($= I_0$), $I_T$ the intensity of the transmission light, $c$ a constant of the lens ($c \div 2R$ where R represents the radius of curvature).

FIG. 4 shows a graph plotted according to equation (1) in which the abscissa shows the quantity of the component insoluble to benzene and the ordinate the quantity of transmission light. As shown in FIG. 4, as the quantity of the component insoluble to benzene decreases, the quantity of light transmission decreases exponentially instead of decreasing linearly as shown by a dotted line. This means that even when the sample is heavily contaminated, a certain quantity of the transmission light can be assured.

As above described, since the quantity of light transmission varies in accordance with the quantity of the component insoluble to benzene it is possible to determine the latter quantity by converting the former into a variable voltage or current by the light receiving member 12.

FIG. 5 is a block diagram of an electric circuit which displays on a meter the electrical signal detected by the light receiving member 12. In FIG. 5, the quantity D of the transmission light is converted into a voltage Vs by the light receiving member 12. After being amplified by an amplifier AP, this voltage Vs is impressed upon the negative input terminal of a phase reverser S, the positive input terminal thereof being impressed with a reversing level voltage $V_L$. Accordingly, the output voltage from the amplifier AP is phase reversed by the phase reverser S with reference to voltage $V_L$ and the output Vc from the phase reverser is displayed by a display meter DS.

The output Vc of the phase reverser S is expressed by the following equation $$Vc = V_L - G \cdot K \cdot P.$$

where K represents the photoelectric conversion coefficient and G the gain of the amplifier AP.

FIG. 6 shows the waveforms of various outputs shown in FIG. 5 wherein curve A shows the output of the photoelectric element 12, curve B the output of the amplifier AP and curve C the output of the phase reverser S when the quantity of the component insoluble to benzene is varied. As can be noted from curve C, as the voltage Vc varies in proportion to $\tau$ is possible to directly display the quantity of the component insoluble to benzene by displaying output voltage Vc by meter DS.

The Vc − c characteristic can be varied by varying the lens constant c, the phase reversing level $V_L$ and the gain G of the amplifier as can be noted from equations (1) and (2).

Figure 7:
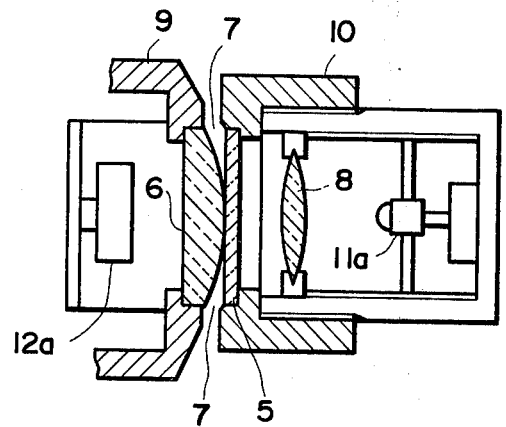
FIG. 7 is a sectional view showing the construction of one example of the optical measuring system embodying the invention.

FIG. 7 shows one example of the optical system employed in the detecting apparatus of this invention, which comprises a luminous element 11a such as an incandescent lamp or a luminous diode, a light receiving member 12a in the form of a solar cell or a CdS cell, a transparent flat plate 5 and a convex lens 6 which are in contact with each other to form a gap 7 for accommodating a liquid sample. Further, a lens 8 is provided for producing parallel light. The convex lens 6 and the light receiving member 12a are supported by a casing 9 whereas the transparent flat plate 5, lens 8 and the luminous element 11a are supported by a casing 10.

Figure 8:
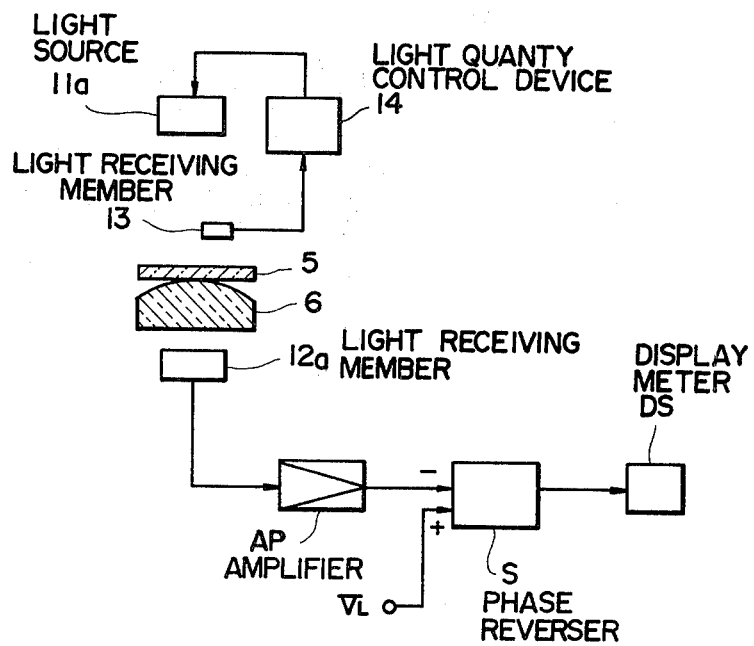
FIG. 8 is a block diagram showing another embodiment of this invention.

FIG. 8 diagrammatically shows another embodiment of this invention which is different from the previous embodiment in that it includes a luminous quantity compensating system which detects the quantity of the light before transmission to always maintain the luminous quantity at a predetermined constant value. Accordingly, the elements same as those of the previous embodiment are designated by the same reference characters.

A light receiving member 13 is disposed close to the transparent flat plate 5 so as to receive light from luminous element 11a or light source and to generate an electric signal proportional to the quantity of the light received. This electric signal is applied to a light quantity control device 14 which is constructed to compensate for the variation in the quantity of the light received by the light receiving member 13. More particularly, the control device 14 controls the light source 11a such that it increases the quantity of the light emission when the quantity of light received by the light receiving member 13 decreases and vice versa, thus always maintaining constant the light quantity emanated by the light source.

Figure 9:
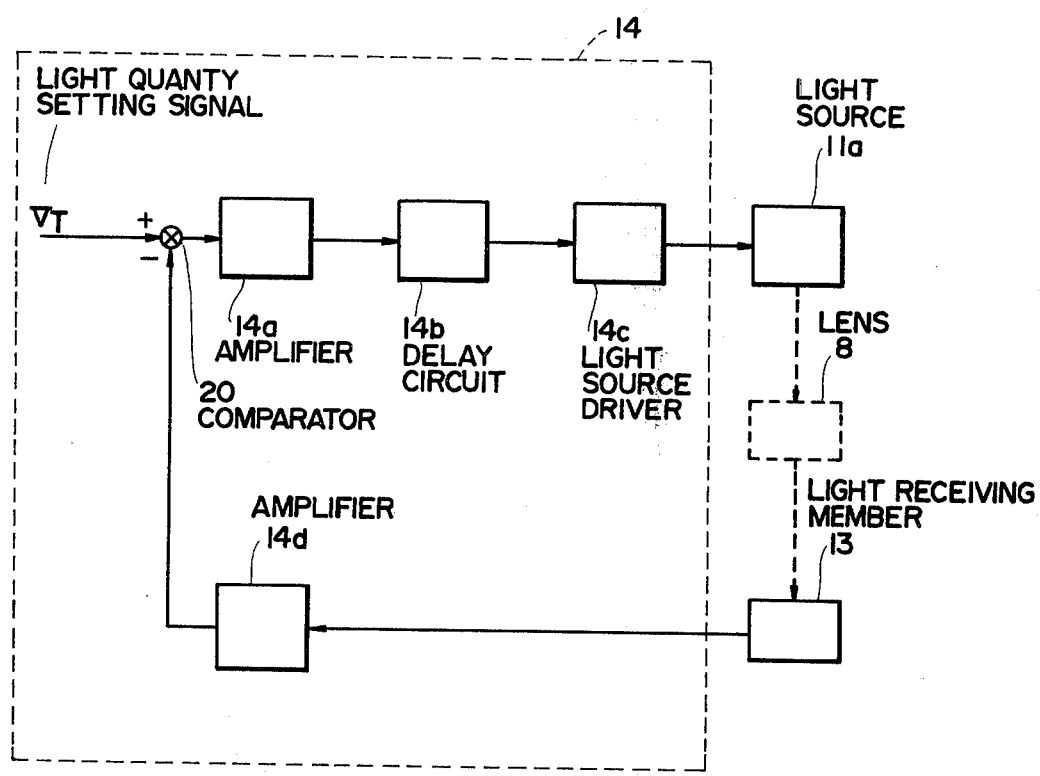
FIG. 9 is a block diagram showing the detail of the light quantity compensating system shown in FIG. 8.

FIG. 9 is a block diagram showing the construction of the luminous quantity compensating system. As shown, the light from the light source 11a is converted into parallel light by lens 8, a portion of the parallel light is received by the second light receiving member 13 and the other portion is passed through the liquid sample as described hereinabove. The light received by the second light receiving member 13 is converted into an electric signal which is amplified by an amplifier 14d and then applied to a comparator 20 to be compared with a reference signal $V_T$ for setting the quantity of light. The differential signal from comparator 20 is applied to a delay circuit 14b through an amplifier 14a and the output of the delay circuit 14b is applied to a light source drive 14c for controlling the current or voltage applied to the light source 11a.

In this manner, the compensating system forming a feedback loop for the luminous quantity operates the light source driver 14c at a level determined by the light quantity setting signal when the luminous quantity of the light source 11a decreases due to degradation thereof thereby always maintaining the luminous quantity at a predetermined constant value. Furthermore, it is possible to adjust the luminous quantity by varying the luminous quantity setting signal thereby enabling measurement at any desired light level. In this manner as light of constant intensity is projected through the liquid sample such as diesel engine oil from the light source 11a it is possible to detect the quantity of the transmission light by the light receiving member 12a correctly and high accuracies. For this reason, it is possible to eliminate the measuring error caused by the unstable condition of the measuring system, that is the difference in the characteristic of the luminous element and the aging thereof.

It should be understood that the compensating system is not limited to that shown in FIG. 9 and that any compensating system may be used so long as it compares the actual luminous quantity with a reference value for controlling the quantity of the light emanated from the light source thus maintaining it at a constant value.

Although a combination of a transparent flat plate and a convex lens was shown for the purpose of forming a gap therebetween having a secondary curve distribution it will be clear that the transparent flat plate may be replaced by a transparent convex body.

What is claimed is:

1. In apparatus for detecting contamination of liquid of the type wherein light emanated by a luminous element is transmitted through a liquid sample and the quantity of the transmitted light is detected by a light receiving member, the improvement which comprises a pair of transparent members interposed between said luminous element and said light receiving member, at least one of said pair of transparent members being convex and in contact with the other at the top of the convex member thus forming therebetween a gap for accommodating a liquid sample.

2. The apparatus according to claim 1 wherein said pair of transparent members comprises a flat glass plate and a convexoplane lens which are held in contact at the top of the convex lens.

3. The apparatus according to claim 1 wherein said light receiving member comprises a photoelectric element for converting the received light into an electric signal, and said apparatus further comprises a phase reverser for reversing the phase of said electric signal and a display member operated by the output from said phase reverser for displaying the degree of contaminaion of said liquid sample.

4. The apparatus according to claim 1 which further comprises a photoelectric converting element for detecting the quantity of light emanated by a light source before the light transmits through said transparent members, means for generating a desired luminous quantity setting signal, means for comparing said setting signal with the output from said photoelectric converting element, and means responsive to the output from said comparing means for controlling the quantity of the light emanated by said light source at a constant value corresponding to said luminous quantity setting signal.

5. The apparatus according to claim 1 which further comprises a first casing containing a light source, a lens for converting the light emanated by the light source into parallel light and a transparent flat plate; a second casing containing a convex lens and a light receiving member located to receive light transmitting through said convex lens; and means for holding said first and second casings in such manner that said transparent flat plate and said convex lens contact with each other for defining a gap therebetween for accommodating a liquid sample to be measured.

* * * * *